United States Patent
Connelly et al.

(10) Patent No.: US 10,634,591 B2
(45) Date of Patent: Apr. 28, 2020

(54) DEVICE FOR CONCENTRATION OF BIOLOGICAL SAMPLE PRIOR TO IMMUNOASSAY

(71) Applicant: Tokitae LLC, Bellevue, WA (US)

(72) Inventors: John Thomas Connelly, Seattle, WA (US); Stephen Paul Harston, Bothell, WA (US); Bernhard Hans Weigl, Seattle, WA (US); Ozgur Emek Yildirim, Bellevue, WA (US)

(73) Assignee: Tokitae LLC, Bellevue, WA (US)

( * ) Notice: Subject to any disclaimer, the term of this patent is extended or adjusted under 35 U.S.C. 154(b) by 469 days.

(21) Appl. No.: 15/457,009

(22) Filed: Mar. 13, 2017

(65) Prior Publication Data
US 2018/0259434 A1 Sep. 13, 2018

(51) Int. Cl.
*G01N 1/40* (2006.01)
*G01N 33/53* (2006.01)
*B01L 3/00* (2006.01)
*B01D 29/92* (2006.01)

(52) U.S. Cl.
CPC ............ *G01N 1/4077* (2013.01); *B01L 3/502* (2013.01); *G01N 33/5302* (2013.01); *B01L 3/5635* (2013.01); *B01L 2200/025* (2013.01); *B01L 2200/0631* (2013.01); *B01L 2300/0681* (2013.01); *B01L 2300/0864* (2013.01); *B01L 2400/0478* (2013.01); *B01L 2400/06* (2013.01); *B01L 2400/0605* (2013.01); *B01L 2400/0633* (2013.01); *B01L 2400/0683* (2013.01); *G01N 2001/4088* (2013.01)

(58) Field of Classification Search
USPC ....... 422/501, 521, 522, 524, 527, 534, 535, 422/546
See application file for complete search history.

(56) References Cited

U.S. PATENT DOCUMENTS

| | | | |
|---|---|---|---|
| 4,347,131 A | 8/1982 | Brownlee | |
| 4,647,376 A * | 3/1987 | Galaj | B01D 61/18 210/257.2 |
| 5,224,489 A | 7/1993 | Guirguis | |
| 5,313,821 A * | 5/1994 | Bett | G01N 1/2214 73/23.34 |
| 6,136,555 A * | 10/2000 | Jones | B01J 19/0046 210/321.6 |

(Continued)

OTHER PUBLICATIONS

PCT International Search Report; International App. No. PCT/US2018/021374; dated Jun. 20, 2018; pp. 1-5.

*Primary Examiner* — Brian R Gordon

(57) ABSTRACT

In some embodiments, a medical-sample filtration device includes: a container including at least one wall forming an internal surface, a first aperture adjacent to a first end of the wall, and a second aperture adjacent to a second end of the wall; a movable insert positioned within the container and including an external surface of a size and shape to reversibly mate with the internal surface of the container; a positioning unit affixed to the internal surface close to the second aperture; a filter unit affixed to the second aperture; a sample conduit affixed to the filter unit; a valve unit attached to the sample conduit; and a connector operable to close the valve when the movable insert is in a predefined position relative to the container.

9 Claims, 14 Drawing Sheets

(56) References Cited

U.S. PATENT DOCUMENTS

| | | | | |
|---|---|---|---|---|
| 7,820,111 | B2* | 10/2010 | Brown | B01L 3/0206 |
| | | | | 422/522 |
| 9,017,621 | B1* | 4/2015 | Zhang | C07H 21/00 |
| | | | | 422/417 |
| 10,080,516 | B2* | 9/2018 | Ellis | A61M 1/36 |
| 2004/0182788 | A1* | 9/2004 | Dorian | B01D 15/02 |
| | | | | 210/649 |
| 2004/0238037 | A1* | 12/2004 | Taylor | E03B 7/006 |
| | | | | 137/364 |
| 2005/0014156 | A1* | 1/2005 | Pawliszyn | G01N 1/40 |
| | | | | 435/7.23 |
| 2006/0141636 | A1* | 6/2006 | Steggles | C12M 33/14 |
| | | | | 436/177 |
| 2010/0297691 | A1* | 11/2010 | Ribeiro | G01N 1/14 |
| | | | | 435/34 |
| 2011/0318843 | A1* | 12/2011 | De Kraker | G01N 31/221 |
| | | | | 436/129 |
| 2015/0004079 | A1* | 1/2015 | Hassouneh | G01N 1/4077 |
| | | | | 422/533 |
| 2015/0072346 | A1* | 3/2015 | Gellibolian | G01N 1/4077 |
| | | | | 435/6.11 |
| 2016/0251628 | A1* | 9/2016 | Vincent | B01D 63/087 |
| | | | | 424/93.7 |
| 2017/0030811 | A1* | 2/2017 | Gellibolian | G01N 1/4077 |
| 2017/0176305 | A1* | 6/2017 | Shi | B03D 1/14 |
| 2017/0274376 | A1* | 9/2017 | Nobile | B01L 3/5023 |
| 2018/0051313 | A1* | 2/2018 | Rajagopal | C12Q 1/04 |

* cited by examiner

FIG. 10
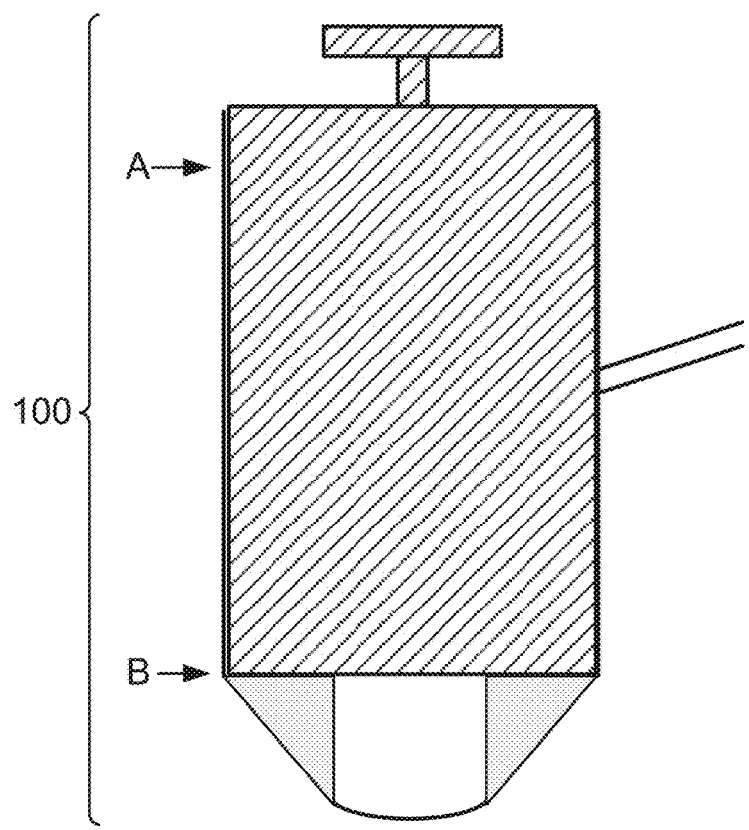
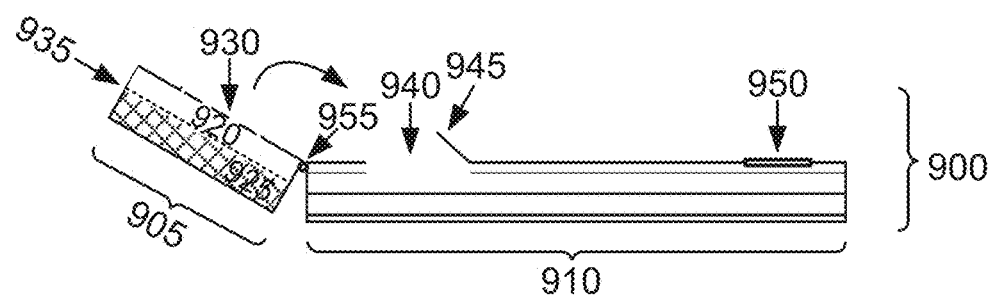

DEVICE FOR CONCENTRATION OF BIOLOGICAL SAMPLE PRIOR TO IMMUNOASSAY

If an Application Data Sheet (ADS) has been filed on the filing date of this application, it is incorporated by reference herein. Any applications claimed on the ADS for priority under 35 U.S.C. § 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In some embodiments, a medical-sample filtration device includes: a liquid-impermeable container including at least one wall forming an internal surface with substantially even cross-sectional dimensions, a first aperture adjacent to a first end of the at least one wall, and a second aperture adjacent to a second end of the at least one wall; a movable insert positioned within the container, the movable insert including an external surface of a size and shape to reversibly mate with the internal surface of the container; a positioning unit affixed to the internal surface of the container at a location adjacent to the second aperture; a filter unit affixed to the second aperture; a sample conduit affixed to the filter unit; a valve unit, including a valve with an open-close switch, operably attached to the sample conduit; and a connector operably connected between the movable insert and the valve unit, the connector operable to close the valve when the movable insert is in a predefined position relative to the container.

In some embodiments; a medical-sample filtration device includes: a liquid-impermeable container including at least one wall forming an internal surface with substantially even cross-sectional dimensions, a first aperture adjacent to a first end of the at least one wall, and a second aperture adjacent to a second end of the at least one wall; a movable insert positioned within the container, the movable insert including an insert section with an external surface of a size and shape to reversibly mate with the internal surface of the container; a sample conduit traversing the movable insert, the sample conduit including a first end within the movable insert; a frangible cover forming a liquid-impermeable seal over the first end of the sample conduit; a positioning unit affixed to the internal surface of the container at a location adjacent to the second aperture; a filter unit affixed to the second aperture; and a piercing conduit traversing the second aperture, the piercing conduit including a first end positioned within the filter unit and distal from the filter, and a second end positioned within an interior of the container, the second end including a piercing surface positioned to intersect with the frangible cover of the movable insert.

In some embodiments, a medical-sample filtration device includes: a liquid-impermeable container including at least one wall forming an internal surface with parallel faces, a first aperture adjacent to a first end of the at least one wall, and a second aperture adjacent to a second end of the at least one wall; a movable insert positioned within the container, the movable insert including an external surface of a size and shape to reversibly mate with the internal surface of the container; the movable insert including a surface of a size, shape and position to transmit force along an axis of the movable insert in a direction from the first aperture to the second aperture; a positioning unit affixed to the internal surface of the container at a location adjacent to the second aperture, the positioning unit of a size and shape to maintain the movable insert at a predetermined position from the second aperture; a filter unit affixed to the second aperture; a immunoassay device including a sample addition region; and a framework securing the liquid-impermeable container adjacent to the immunoassay, the framework including a first position with the second aperture positioned adjacent to a waste region of the immunoassay device and a second position with the filter unit positioned adjacent to the sample addition region of the immunoassay.

In some embodiments, a medical-sample filtration device includes: a liquid-impermeable container including at least one wall forming an internal surface with substantially even cross-sectional dimensions, a first aperture adjacent to a first end of the at least one wall, and a second aperture adjacent to a second end of the at least one wall; a movable insert positioned within the container, the movable insert including an external surface of a size and shape to reversibly mate with the internal surface of the container, the movable insert including a surface of a size, shape and position to transmit force along an axis of the movable insert in a direction from the first aperture to the second aperture; a positioning unit affixed to the internal surface of the container at a location adjacent to the second aperture; a conduit affixed to the second aperture of the container; a filter unit affixed to the conduit; a frangible cover forming a liquid-impermeable seal over an end of the conduit distal to the filter unit; and a piercing conduit, the piercing conduit including a first end affixed to a surface of the movable insert, and a second end including a piercing surface positioned to traverse the frangible cover.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 10 is a schematic of a medical-sample filtration device.

DETAILED DESCRIPTION

Figure 1:
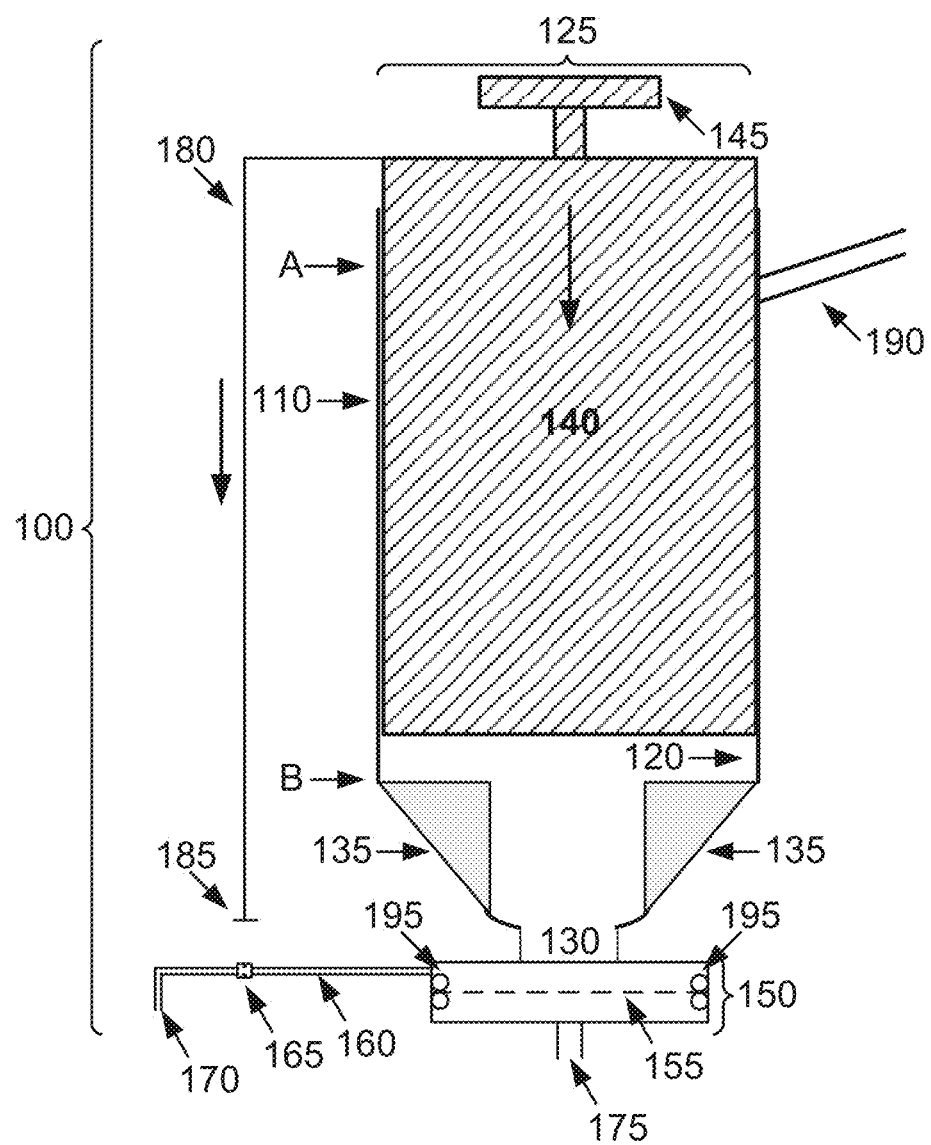
FIG. 1 is a schematic of a medical-sample filtration device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Medical diagnostic tests such as immunoassays can detect small quantities of analytes in a liquid sample. Many diagnostic assays utilize samples including blood, saliva, urine, and wound exudates from individual patients. These samples can be collected through a variety of means with varying levels of invasiveness to the patient. Liquid samples made available through non-invasive means are often preferred in clinical settings for ease of use and avoidance of infection hazards to the patient as well as healthcare personnel. An analyte present in a liquid sample is often, although not always, chemically available for binding or similar assays. In some situations, a liquid sample is utilized in an immunoassay, which can be a lateral flow assay (LFA). In some situations, a liquid sample from a patient can be overly dilute and the analyte must be concentrated in some manner prior to analysis. For example, blood samples are often centrifuged prior to further testing.

Urine is a readily available bodily fluid that can be valuable for medical testing for a variety of analytes. For example, urine can contain lipoarabinomannan (LAM), a glycolipid associated with the pathogen *Mycobacterium tuberculosis*. Urine is non-invasively available and can be obtained from a wide spectrum of patients. The utility of urine as a diagnostic liquid sample can be impacted, however, by a variation in levels of dilution depending on the health status of an individual patient as well as factors such as their recent ingestion history and activities. Some analytes, such as LAM, may be present in undetectable concentrations in a liquid sample direct from a patient, but readily detected when the analyte is concentrated in a subsample. For such analytes, a medical-sample filtration device can be utilized prior to analysis in a diagnostic assay, such as an immunoassay.

In some embodiments, a medical-sample filtration device includes: a liquid-impermeable container including at least one wall forming an internal surface with substantially even cross-sectional dimensions, a first aperture adjacent to a first end of the at least one wall, and a second aperture adjacent to a second end of the at least one wall; a movable insert positioned within the container, the movable insert including an external surface of a size and shape to reversibly mate with the internal surface of the container; a positioning unit affixed to the internal surface of the container at a location adjacent to the second aperture; a filter unit affixed to the second aperture; a sample conduit affixed to the filter unit; a valve unit, including a valve with an open-close switch, operably attached to the sample conduit; and a connector operably connected between the movable insert and the valve unit, the connector operable to close the valve when the movable insert is in a predefined position relative to the container.

FIG. 1 illustrates aspects of a medical-sample filtration device. A device such as the one depicted in FIG. 1 can be used, for example, to concentrate LAM in a urine sample. In some embodiments, the urine may have a buffer or other liquid added prior to use in the medical-sample filtration device, for example a buffer calibrated to modify the salt concentration in the resulting filtrate. A medical-sample filtration device as described herein concentrates analyte(s) of a size above a filter cutoff size and also removes excess water content from the liquid sample. A medical-sample filtration device as described herein utilizes physical pressure on the liquid sample in order to force particles below a predetermined size through a filter for removal. For example, in some embodiments a liquid sample is subjected to 30 psi pressure within the device. For example, in some embodiments a liquid sample is subjected to 60 psi pressure within the device. For example, in some embodiments a liquid sample is subjected to a pressure between 30 psi pressure and 60 psi of pressure within the device.

The medical-sample filtration device 100 illustrated in FIG. 1 includes a liquid-impermeable container including a wall 110, the wall 110 forming an internal surface 120 with substantially even cross-sectional dimensions. In the embodiment illustrated in FIG. 1, the wall 110 is shaped as a cylinder (illustrated in substantial cross-section in FIG. 1). The wall 110 correspondingly has an internal surface 120 that corresponds to a cylindrical shape. In some embodiments, the internal surface of the container is formed as a cylindrical structure. In some embodiments, the container includes a substantially smooth internal surface. In some embodiments, the wall and corresponding surface is circular in cross-section. The wall 110 of the container has a first aperture 125 opening to the top of the device 100 as shown in FIG. 1. The wall 110 of the container has a second aperture 130 which in the view of FIG. 1 is positioned adjacent to a filter unit 150.

A movable insert 140 is positioned within the cylindrical wall 110. The movable insert 140 has an external surface of a size and shape to reversibly mate with the internal face of the wall 110. In some embodiments, the movable insert is shaped as a cylindrical structure. The external surface of the movable insert 140 and the inner surface 120 of the wall 110 are of a size, shape and position so that the movable insert 140 can move along an axis of the container, shown as top to bottom in the view of FIG. 1, with minimal space between the surfaces. In some embodiments, there may be a gasket or similar structure positioned at a region between the surfaces. The movable insert 140 is fabricated in a manner and from a material with sufficient strength to move with sufficient pressure through the container from the first aperture 125 to the second aperture 130 to meet the needs of the embodiment (e.g. a pressure between 30 psi pressure and 60 psi of pressure). In some embodiments, the movable insert is of a size, shape and position to transmit a force of at least 50 psi toward the second aperture. In some embodiments, the movable insert is of a size, shape and position to transmit a force of at least 80 psi toward the second aperture. In some embodiments, the movable insert is of a size, shape and position to transmit a force of at least 100 psi toward the second aperture. In some embodiments, the movable insert is of a size, shape and position to transmit a force of at least 120 psi toward the second aperture. In some embodiments, the movable insert includes a pressure application region of a size, shape and position to transmit force against a surface of the movable insert and along an axis of the insert substantially parallel with the external surface of a size and shape to reversibly mate with the internal surface of the container. In the embodiment illustrated in FIG. 1 the movable insert 140 includes a pressure application region 145 that is affixed to the movable insert 140 at the end of the movable insert 140 positioned adjacent to the first aperture 125 of the container.

A positioning unit is affixed to the internal surface of the container at a location adjacent to the second aperture. FIG. 1 depicts an embodiment wherein the positioning unit 135 has a triangular cross-section. The positioning unit can include a face of a size and shape to mate with an exterior surface of the movable insert at a position distal to the second aperture of the container. In some embodiments, the positioning unit is of a size, shape and position to form a space of a predetermined volume adjacent to the second aperture and below a top face of the positioning unit. For example, in the embodiment illustrated in FIG. 1, the movable insert 140 has a bottom face positioned toward the second aperture 130 (e.g. lower in the view of FIG. 1). The bottom face of the movable insert 140 can move between a first position near the top aperture 125 of the container, the first position marked "A" in FIG. 1, to a second position in contact with a surface of the positioning unit 135 and marked as position "B." When the movable insert 140 is positioned in contact with the positioning unit 135, there is a volume adjacent to the positioning unit 135 and the second aperture 130. In some embodiments, this is a space of a predefined size that holds, for example, an appropriate volume of fluid as required for a downstream assay.

A filter unit is affixed to the second aperture of the medical-sample filtration device. In some embodiments, a filter unit includes: a filter; and a holder securing the filter in place; wherein the sample conduit is affixed to the filter unit at a position between the filter and the second aperture of the container. In some embodiments, the filter is a size-exclusion membrane. For example, in an embodiment intended for use to concentrate a urine sample while retaining LAM in the final concentrated sample, the filter can be a 5K Dalton size exclusion membrane. Some embodiments include a size-exclusion membrane positioned and affixed to an interior of the filter unit. Some embodiments include: a size-exclusion membrane; and a holder securing the membrane in place. Some embodiments include a support for the filter, such as a mesh or perforated sheet structure of a size, shape and position to provide physical support for the filter. For example a support can be of a strength and position to secure an otherwise flexible membrane in position for use within a filter unit, and maintain the position during use (e.g. during periods of pressure).

In the embodiment illustrated in FIG. 1; the filter unit 150 is affixed to the second aperture 130 of the container so that fluid forced through the second aperture 130 from the pressure exerted toward it by the movable insert 140 is directed against a surface of the filter 155 within the filter unit 150. A holder 195 secures the filter 155 in place within the filter unit 150. The filter 155 is positioned within the holder 195 at a position substantially along the midline of the housing of the filter unit 150. A waste conduit 175 is positioned distally to the attachment to the container. There is also a sample conduit 160 attached to the filter unit 150 at a position adjacent to the face of the filter 155 adjacent to the container. The sample conduit 160 is positioned to permit fluid flow from the side of the filter closer to the container holding the pre-filtered sample. In some embodiments, the sample conduit is a tubular structure.

A valve unit 165 including a valve with an open-close switch is operably attached to the sample conduit 160. The valve unit 165 includes a valve operably attached to the sample conduit 160 so that the valve can open and close to permit or exclude fluid from moving through the valve. In some embodiments, the valve unit includes a binary open/close valve. In some embodiments, the valve unit includes a reversible valve. In some embodiments, the valve unit includes a valve that is a single use valve, which cannot be closed again once it is opened. For example, the valve can include a breakable or bendable component that cannot be returned to its original configuration. In some embodiments, the interior volume of the positioning unit, the filter unit, and the sample conduit prior to the valve unit is a predetermined volume for analysis. For example, the interior volumes of these components taken together can be an appropriate volume for analysis in an immunoassay. A sample dispensation end 170 is part of the sample conduit 160 at a position distal to the valve unit 165.

A connector is operably connected between the movable insert and the valve unit, the connector operable to close the valve when the movable insert is in a predefined position relative to the container. In some embodiments, the connector is an electronic connector. In some embodiments, the connector is a mechanical connector. In the embodiment shown in FIG. 1, a connector 180 is attached at a top edge to the top edge of the movable insert, and includes a second end at a position distal to the attachment to the movable insert, the second end in a position adjacent to the valve unit when the movable insert has moved to an appropriate position. In some embodiments there is a pressure transmitting device attached to the connector. For example, FIG. 1 illustrates a pressure transmitting device 185 that includes a plate attached to the distal end of the connector 180 and positioned to come into contact with the valve unit 165 and put pressure on the surface of the valve unit 165 when the movable insert 140 is positioned adjacent to the positioning unit 135 within the container.

Some embodiments include a sample addition aperture in the wall of the container at a position adjacent to the first aperture, and a sample addition conduit affixed to an exterior surface of the container, surrounding the sample addition aperture. The embodiment illustrated in FIG. 1 includes a sample addition aperture on the top right of the container in the view of the figure, and a sample addition conduit 190 operably affixed to the container and surrounding the aperture. The sample addition conduit can be of a size, shape and position so that a liquid sample, for example urine, can be added to the container when the movable insert is in an extended position, for example adjacent to position A in FIG. 1. The sample addition conduit can be of a size, shape and position so that addition of a liquid sample is blocked by the side of the movable insert when the movable insert has been pressed down against the fluid in the container, for example in the configuration as illustrated in FIG. 1.

Some embodiments include a fluid metering container affixed to the sample conduit distal to the valve, wherein the fluid metering container includes an internal region of a size to contain a sample volume, and an overflow conduit positioned to remove excess fluid from the internal region. For example, a fluid metering container can be of a size, shape and position to meter out and hold a predetermined volume of filtered fluid as needed for a downstream assay, such as an immunoassay. An overflow conduit can be attached to the fluid metering container, the overflow conduit of a size, shape and position to remove excess fluid beyond a metered amount held in the fluid metering container. The overflow conduit can, for example, be attached to or include a, waste container. The overflow conduit can, for example, be attached between a first fluid metering container and a second fluid metering container, and positioned to move excess fluid from the first container into the second container.

Some embodiments include an immunoassay operably attached to the sample conduit. For example, in the embodiment illustrated in FIG. 1, the sample dispensation end 170 that is part of the sample conduit 160 at a position distal to the valve unit 165 can be attached to an immunoassay. The immunoassay can include a disposable single use assay, such as a paper-based assay, a lateral flow assay, and/or a vertical flow assay.

Figure 2:
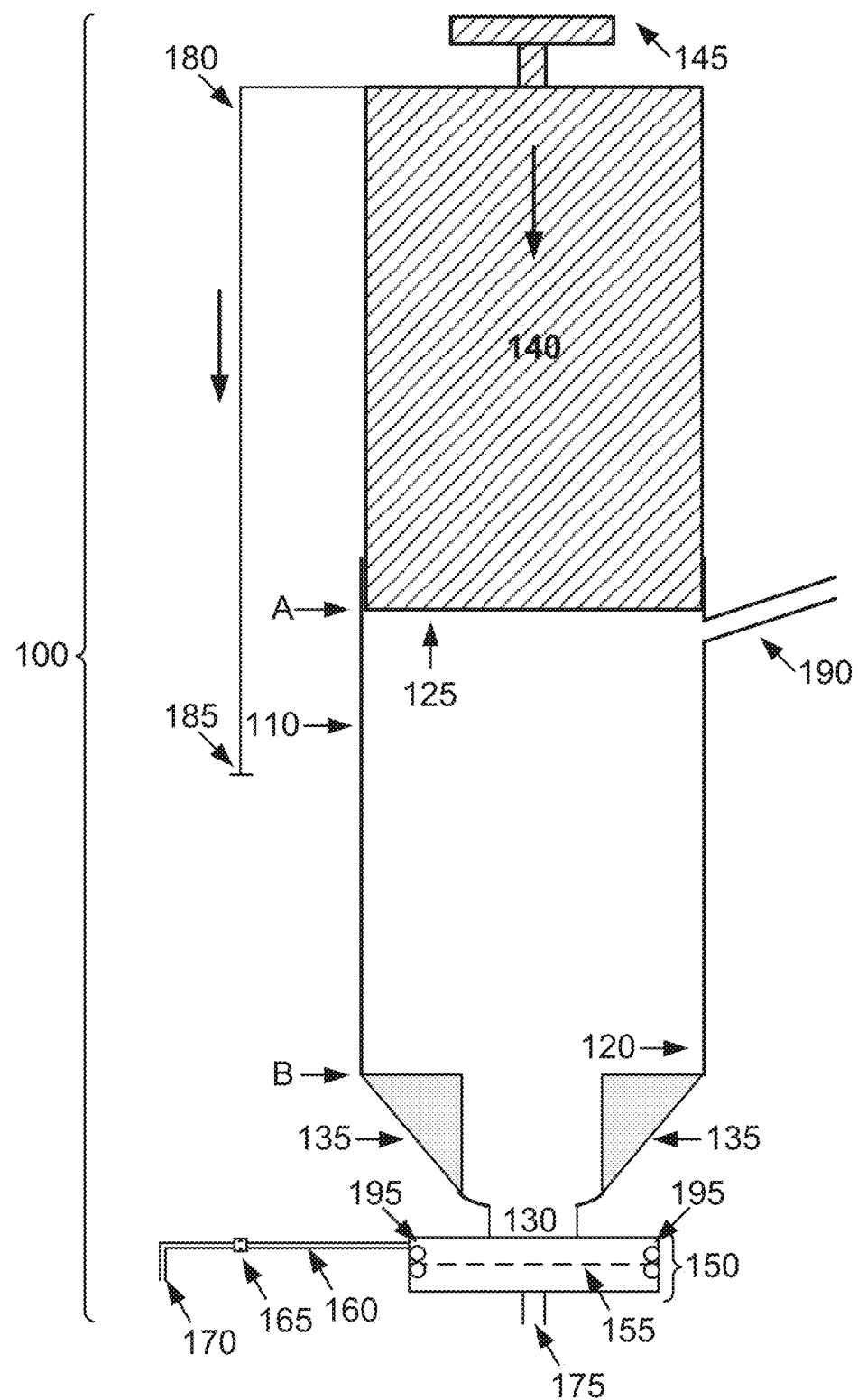
FIG. 2 is a schematic of a medical-sample filtration device.

FIG. 2 illustrates a configuration of a medical-sample filtration device 100 similar to the device illustrated in FIG. 1. In the configuration shown, the movable insert 140 is positioned so that the lower face of the insert is adjacent to position A on the container wall 110. This configuration would permit a medical fluid sample, such as urine, to enter the container through the sample addition conduit 190 attached to the upper wall 110 of the container.

Figure 3:
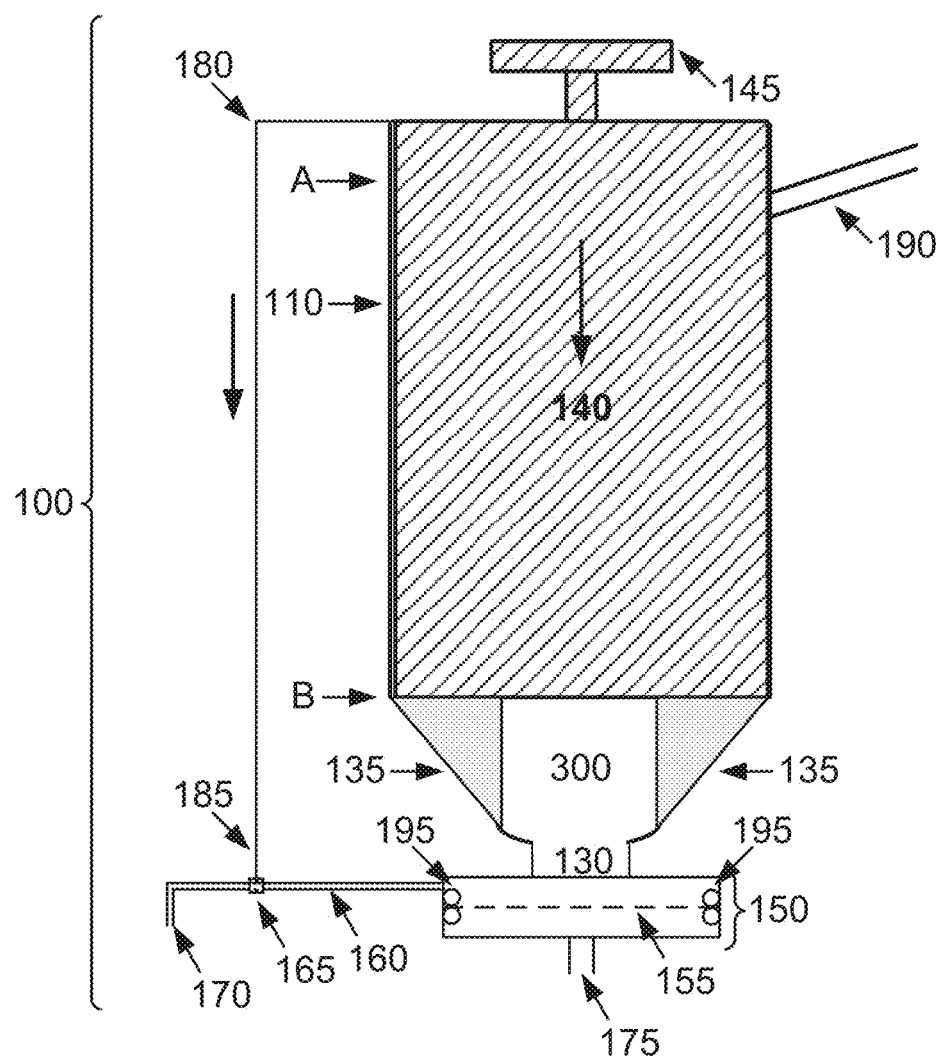
FIG. 3 is a schematic of a medical-sample filtration device.

FIG. 3 depicts a configuration of a medical-sample filtration device 100 similar to the devices illustrated in FIGS. 1 and 2. In the configuration illustrated, the movable insert 140 has been pushed down, as depicted by the downward facing arrows, so that the lower edge of the movable insert 140 is adjacent to the lower position B on the wall 110 of the container. Additional fluid cannot pass into the container through the sample addition conduit 190 attached to the upper wall 110 of the container as the side of the movable insert 140 blocks the aperture in the wall 110 that the sample addition conduit 190 surrounds. The lower face of the movable insert 140 is in contact with the upper edge of the positioning unit 135. The size and shape of the positioning unit 135 within the lower portion of the container forms a sample space 300 of a predetermined size. Depending on the embodiment, the sample space can be, for example, between 100 microliters and 500 microliters. Depending on the embodiment, the sample space can be, for example, between 100 microliters and 1 milliliter (mL). Depending on the embodiment, the sample space can be, for example, between 500 microliters and 2 milliliter. Depending on the embodiment, the sample space can be, for example, between 1 milliliter and 5 milliliters.

FIG. 3 also depicts that the pressure transmitting device 185 attached to the distal end of the connector 180 is in contact with the top face of the valve unit 165 in the configuration illustrated. Pressure from contact with the pressure transmitting device 185 can, for example, toggle a mechanical switch within the valve unit 165, causing the valve to open and a sample fluid to flow through the valve unit 165. Pressure from contact with the pressure transmitting device 185 can, for example, trigger an electronic switch within the valve unit 165, causing the valve to open and a sample fluid to flow through the valve unit 165.

In some embodiments, a medical-sample filtration device includes: a liquid-impermeable container including at least one wall forming an internal surface with substantially even cross-sectional dimensions, a first aperture adjacent to a first end of the at least one wall, and a second aperture adjacent to a second end of the at least one wall; a movable insert positioned within the container, the movable insert including an insert section with an external surface of a size and shape to reversibly mate with the internal surface of the container; a sample conduit traversing the movable insert, the sample conduit including a first end within the movable insert; a frangible cover forming a liquid-impermeable seal over the first end of the sample conduit; a positioning unit affixed to the internal surface of the container at a location adjacent to the second aperture; a filter unit affixed to the second aperture; and a piercing conduit traversing the second aperture, the piercing conduit including a first end positioned within the filter unit and distal from the filter, and a second end positioned within an interior of the container, the second end including a piercing surface positioned to intersect with the frangible cover of the movable insert.

Figure 4:
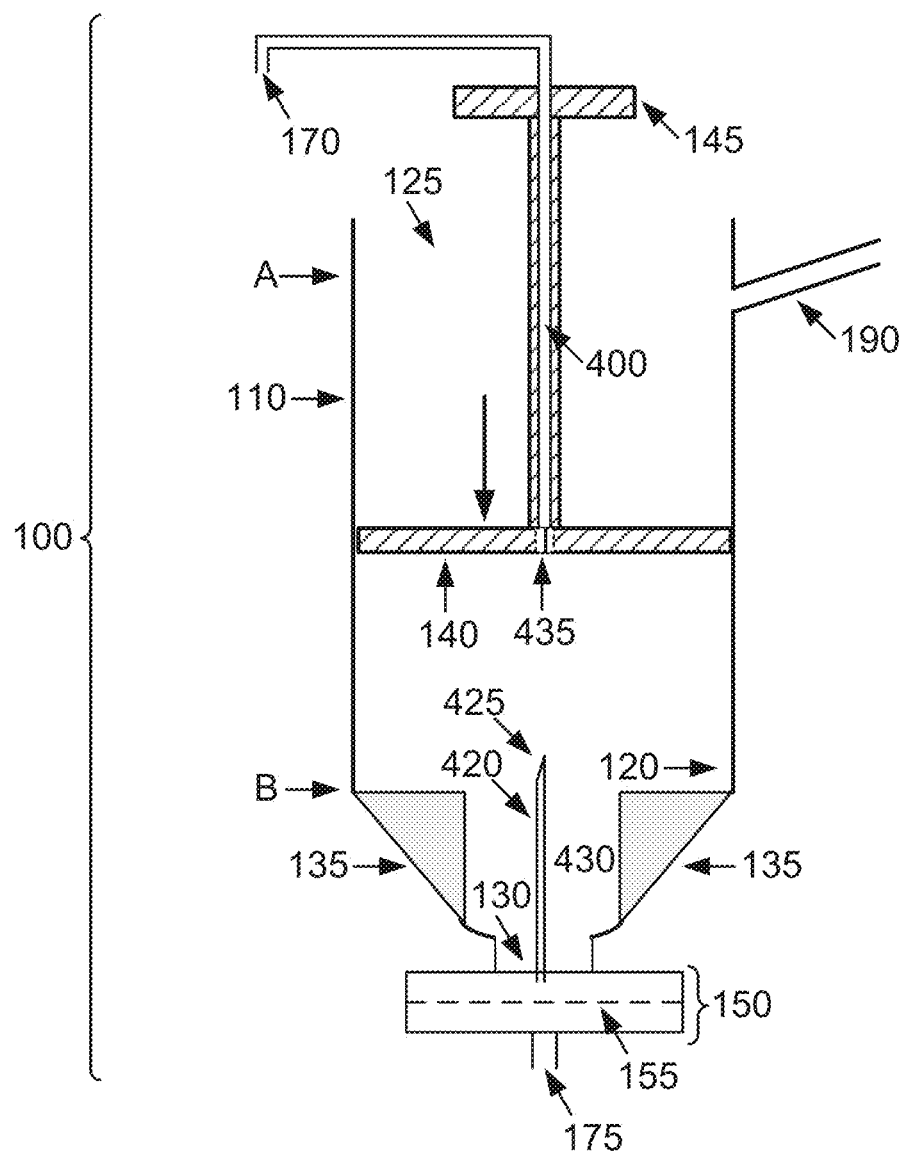
FIG. 4 is a schematic of a medical-sample filtration device.

FIG. 4 illustrates aspects of a medical-sample filtration device 100. The device 100 includes a liquid-impermeable container including a wall 110 forming an internal surface 120 with substantially even cross-sectional dimensions. The container includes a first aperture 125 positioned at the top of the wall 110 and a second aperture 130 positioned at the bottom edge of the wall 110. In some embodiments, the internal surface of the container is shaped as a cylindrical structure. In some embodiments, the container has a substantially smooth internal surface for all or part of the internal surface region of the container.

A movable insert 140 is positioned within the container so that the interior surface of the container wall 110 is in contact with the outer surface of the movable insert 140. In some embodiments, the movable insert includes a gasket or similar feature adjacent to the outer surface. In some embodiments, the movable insert is shaped as a cylindrical structure. In some embodiments, the movable insert includes a pressure application region of a size, shape and position to transmit force against a surface of the movable insert and along an axis of the insert substantially parallel with the external surface of a size and shape to reversibly mate with the internal surface of the container. The device embodiment illustrated in FIG. 4 includes a pressure application region 145 affixed to the movable insert 140. The movable insert can be of a size, shape and position to transmit force from the pressure application region. In some embodiments, a movable insert is of a size, shape and position to transmit a force of at least 50 psi toward the second aperture.

A sample conduit is positioned within the movable insert and traverses the movable insert. In some embodiments, a sample conduit traverses an axis of the movable insert. In some embodiments, a sample conduit is a tubular structure. FIG. 4 illustrates that a sample conduit 400 traverses the length of the movable insert 140 (up and down in the view point of the Figure). In some embodiments, the sample conduit is fully or substantially hollow. In some embodiments, the sample conduit can further include one or more filters, meshes, or porous materials. The sample conduit includes a first end within the movable insert. In some embodiments, such as illustrated in FIG. 4, the sample conduit 400 traversing the movable insert 140 traverses an axis of the movable insert 140. For example the sample conduit can traverse a long axis of the movable insert and accordingly be positioned in parallel with the walls of the container. The sample conduit continues through the movable insert and terminates with a sample dispensation end exterior to the device. For example in FIG. 4 the sample conduit 400 traverses the movable insert 140 and the pressure application region 145, to terminate with a sample dispensation end 170 external to the device and positioned distal to the outer edge of the container. Some embodiments further include an immunoassay operably attached to the sample conduit, for example at a sample dispensation end exterior to the device.

A frangible cover forms a liquid-impermeable seal over the first end of the sample conduit. FIG. 4 illustrates an embodiment with a frangible cover 435 forming a seal over the end of the sample conduit 400 attached to the movable insert 140 at the surface positioned within the interior of the container. In the illustrated embodiment, the sample conduit includes a first end affixed to the frangible cover and a second end positioned exterior to the device. A frangible cover can be of a size, shape and position to be breached by a piercing conduit.

A medical-sample filtration device includes a positioning unit affixed to the internal surface of the container at a location adjacent to the second aperture. FIG. 4 illustrates an embodiment wherein the container width narrows adjacent to the second aperture 130, and a positioning unit 135 is affixed to the interior of the container adjacent to the second aperture 130. In some embodiments, the positioning unit includes a top face of a size and shape to mate with an exterior surface of the movable insert. In some embodiments, the positioning unit is of a size, shape and position to form a space of a predetermined volume adjacent to the first end of the piercing conduit and below a top face of the positioning unit. A space of a predetermined volume 430 is shown in FIG. 4.

A filter unit is affixed to the second aperture of the container. The embodiment illustrated in FIG. 4 includes a filter unit 150. A filter 155 is positioned within the filter unit 150. Some embodiments of a filter unit include a filter, and a holder securing the filter in place. Some embodiments of a filter unit include a filter, wherein the filter is a size-exclusion membrane. Some embodiments of a filter unit include a filter, wherein the filter is a size-exclusion membrane, and a holder securing the membrane in place. Some embodiments of a filter unit include a filter, wherein the filter is a size-exclusion membrane, and a support structure adjacent to the membrane. In some embodiments, a waste conduit is affixed to the filter unit, which can be at a side distal to the filter from the container. FIG. 4 illustrates a filter unit 150 with an attached waste conduit 175, wherein the waste conduit 175 is positioned distal to the container holding the pre-filtered sample, so that fluid that flows through the filter 155 can be removed from the filter unit 150 through the waste conduit 175.

A medical-sample filtration device includes a piercing conduit traversing the second aperture of the container. A piercing conduit includes a first end positioned within the filter unit and distal from the filter, and a second end positioned within the interior of the container, the second end including a piercing surface positioned to intersect with the frangible cover of the movable insert. FIG. 4 illustrates an embodiment with a piercing conduit 420 formed as a hollow needle, similar to an injection needle. The piercing conduit 420 includes a piercing surface 425 positioned at a location in alignment with the frangible cover 435 of the movable insert 140. The piercing conduit includes a first end affixed to the filter unit 150, with an open first end of the hollow conduit positioned adjacent to the filter 155 within the filter unit 150. There is a gap within the filter unit 150 between the open end of the hollow piercing conduit 420 and the surface of the filter 155. In some embodiments, the piercing conduit is of a size, shape and position so that the piercing surface is adjacent to the first end of the sample conduit when the movable insert is in contact with the positioning unit. In some embodiments, the piercing conduit is of a size, shape and position so that the piercing surface is within the first end of the sample conduit when the movable insert is in contact with the positioning unit.

In some embodiments of a medical-sample filtration device, the interior volume of the positioning unit, the filter unit, and the piercing conduit is a volume corresponding to a predicted analysis sample volume. For example, during use, fluid will be placed in the interior of the container and then forced through the filter unit. If the filter unit includes a size-exclusion filter, the majority of an analyte of interest will be retained in the space prior to the filter, or within the predicted analysis sample volume. For example, FIG. 4 includes a space of a predetermined volume 430 adjacent to the second aperture 130 of the container and the positioning unit 135.

Some embodiments of a medical-sample filtration device include a sample addition aperture in the wall of the container at a position adjacent to the first aperture; and a sample addition conduit affixed to an exterior surface of the container, surrounding the sample addition aperture. For example, FIG. 4 includes a sample addition conduit 190 affixed to the wall 110 of the container at a position adjacent to the first aperture 125 of the container.

Figure 5:
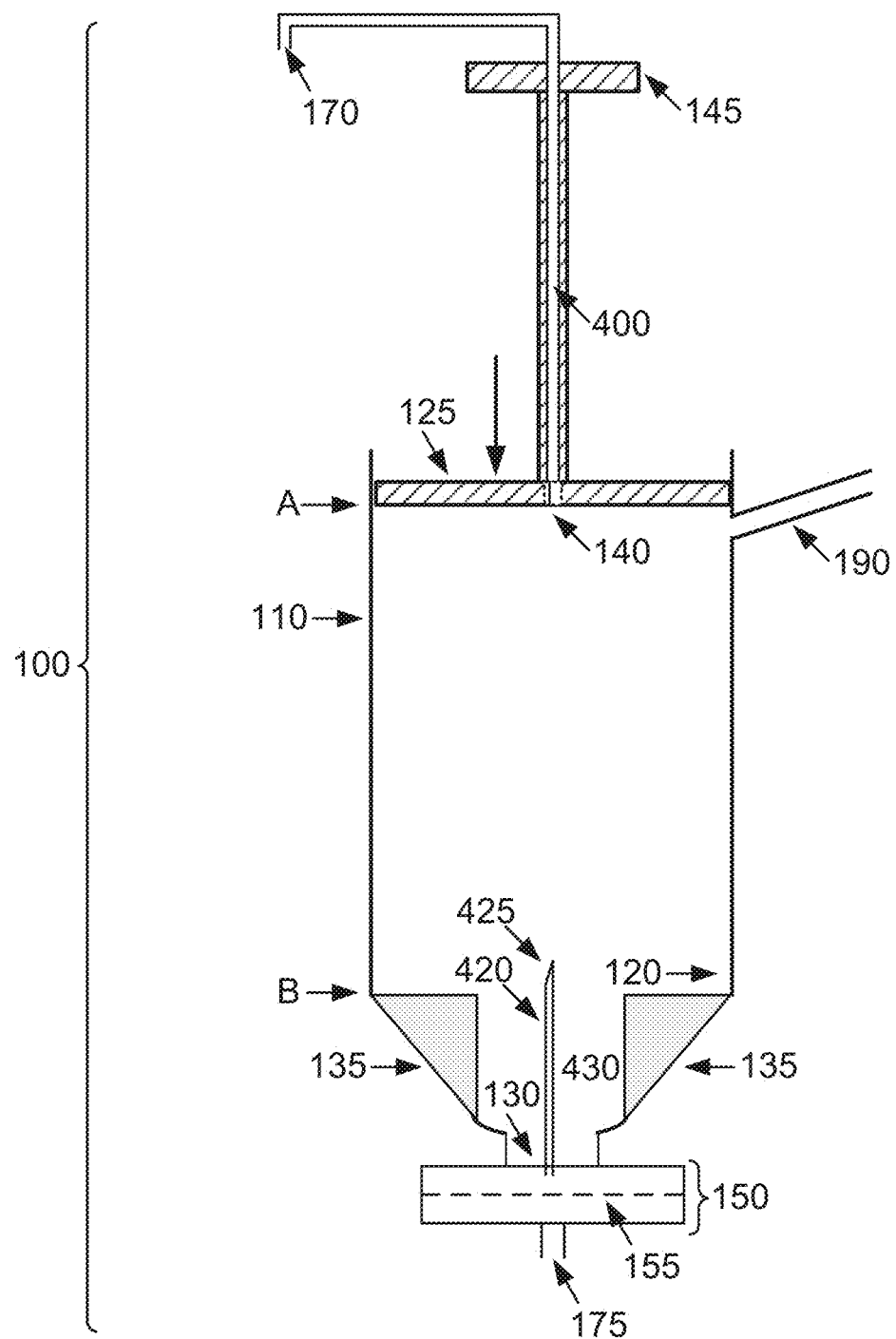
FIG. 5 is a schematic of a medical-sample filtration device.

FIG. 5 illustrates aspects of an embodiment of a medical-sample filtration device similar to the one illustrated in FIG. 4. In the view of FIG. 5, the movable insert 140 is at a position within the container where a liquid sample can enter the interior of the container through the sample addition conduit 190. The face of the movable insert 140 positioned within the container is at a point distal to the positioning unit 135 and above the top of the sample addition conduit 190 (marked as position A). During use, while the device is in this configuration, a liquid sample may be added to the interior of the container through the sample addition conduit. After a liquid sample is added, pressure can be applied to the movable insert 140, possibly via the pressure application region 145, so that the movable insert 140 slides within the container to a position adjacent to the positioning unit 135.

Figure 6:
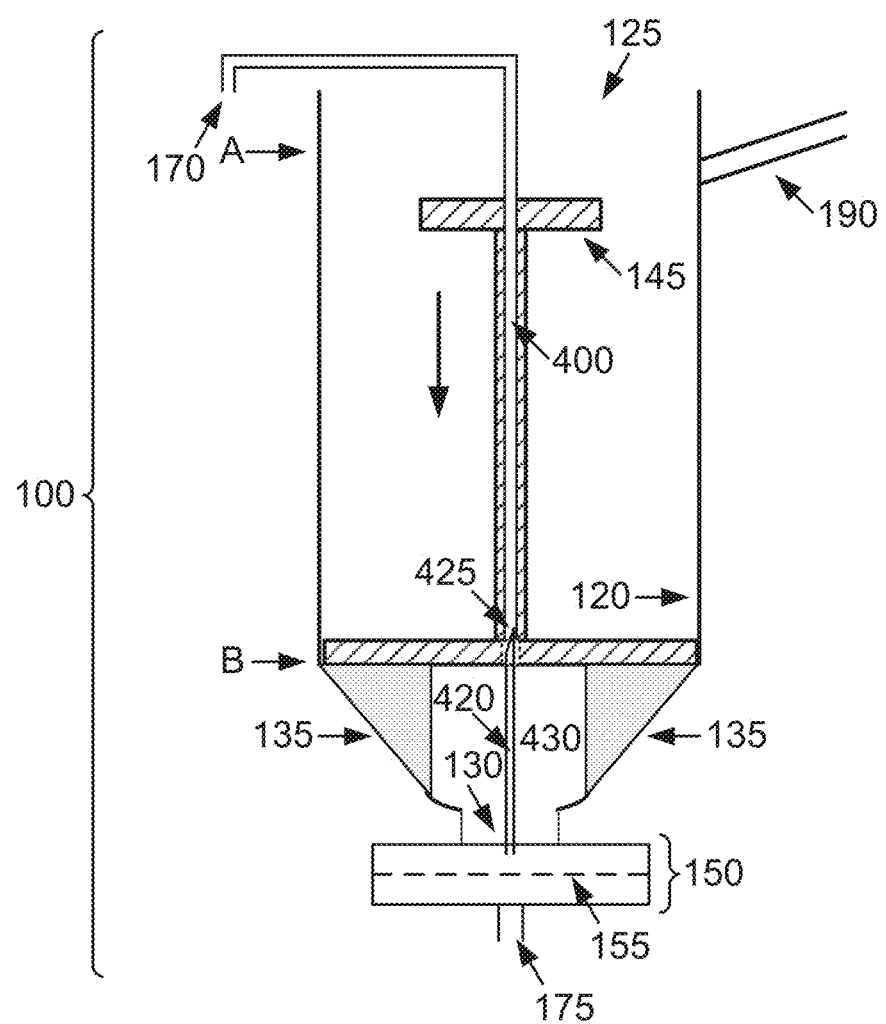
FIG. 6 is a schematic of a medical-sample filtration device.

FIG. 6 depicts aspects of an embodiment of a medical-sample filtration device similar to the ones illustrated in FIGS. 4 and 5. In the view of FIG. 6, the movable insert 140 has been pressed downward within the container from a position adjacent to the first aperture 125 (e.g. as shown in FIG. 5) and is in a position where the face of the movable insert is in contact with the positioning unit 135. The movable insert 140 is positioned at location B, proximal to the second aperture. In this position, the piercing surface 425 of the hollow piercing conduit 420 has punctured the frangible cover 435 of the movable insert 140. The piercing conduit 420 forms a conduit from the interior of the filter unit 150 adjacent to a surface of the filter 155 facing the second aperture 130 of the container. In this position; much of a sample fluid has been forced through the filter 155 of the filter unit, and the fluid remaining in the top portion of the filter unit and the sample volume 430 includes elevated, or concentrated, levels of an analyte of interest. Once the hollow piercing conduit 420 has punctured the frangible cover 435 of the movable insert 140, as illustrated in FIG. 6, the concentrated sample fluid can be released from the device through the piercing conduit 420 and the sample conduit 400, to the sample dispensation end 170 external to the device 100.

Some embodiments of a medical-sample filtration device include: a liquid-impermeable container including at least one wall forming an internal surface with parallel faces, a first aperture adjacent to a first end of the at least one wall, and a second aperture adjacent to a second end of the at least one wall; a movable insert positioned within the container, the movable insert including an external surface of a size and shape to reversibly mate with the internal surface of the container, the movable insert including a surface of a size, shape and position to transmit force along an axis of the movable insert in a direction from the first aperture to the second aperture; a positioning unit affixed to the internal surface of the container at a location adjacent to the second aperture, the positioning unit of a size and shape to maintain the movable insert at a predetermined position from the second aperture; a filter unit affixed to the second aperture; a immunoassay device including a sample addition region; and a framework securing the liquid-impermeable container adjacent to the immunoassay, the framework including a first position with the second aperture positioned adjacent to a waste region of the immunoassay device and a second position with the filter unit positioned adjacent to the sample addition region of the immunoassay.

Figure 7:
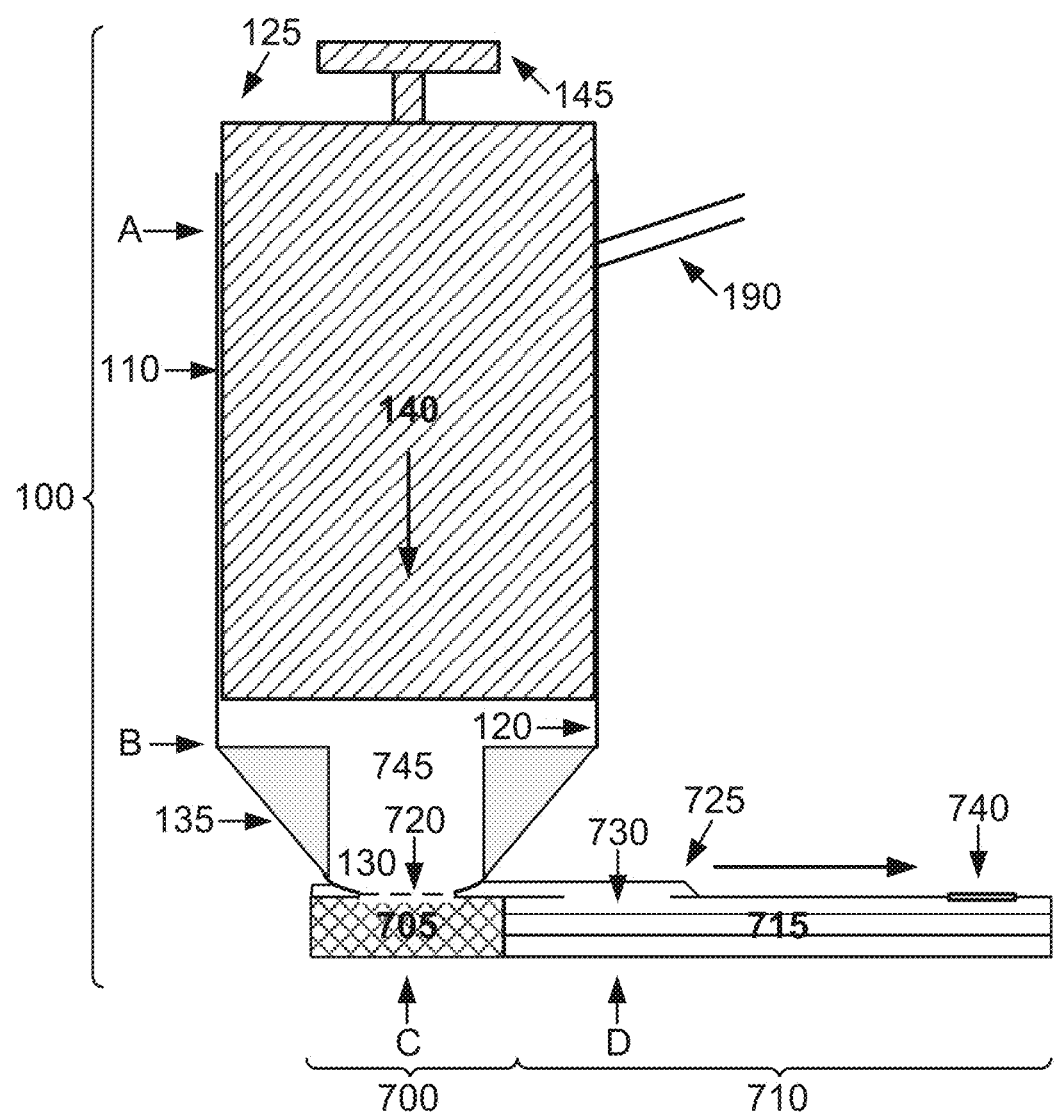
FIG. 7 is a schematic of a medical-sample filtration device.

FIG. 7 illustrates aspects of a medical-sample filtration device 100. The medical-sample filtration device 100 includes a liquid-impermeable container including a wall 110 forming an internal surface 120 with parallel faces. In some embodiments, the internal surface 120 is a cylindrical structure. In some embodiments the internal surface 120 is a substantially smooth surface. The liquid-impermeable container has a first aperture 125 adjacent to a first end of the wall 110, and a second aperture 130 adjacent to a second end of the wall 110.

A movable insert 140 is positioned within the container, the movable insert 140 including an external surface of a size and shape to reversibly mate with the internal surface 120 of the container. In some embodiments, the external surface of the movable insert 140 is a cylindrical structure. The movable insert 140 includes a surface of a size, shape and position to transmit force along an axis of the movable insert 140 in a direction from the first aperture 125 to the second aperture 130 top to bottom in the view of FIG. 7). In some embodiments, the movable insert 140 includes a pressure application region 145 of a size, shape and position to transmit force against a surface of the movable insert 140 and along an axis of the insert 140 substantially parallel with the external surface of a size and shape to reversibly mate with the internal surface 120 of the container. In some embodiments, the movable insert 140 is of a size, shape and position to transmit a force of at least 50 psi toward the second aperture.

The medical-sample filtration device 100 also includes a positioning unit 135 affixed to the internal surface 120 of the container at a location adjacent to the second aperture 130. The positioning unit 135 is of a size and shape to maintain the movable insert 140 at a predetermined position from the second aperture 130. For example, the positioning unit can include a face with a surface of a size, shape and position to mate with a surface of a face of the movable insert. The positioning unit can include a face of a size and shape to mate with an exterior surface of the movable insert at a position distal to the second aperture of the container. In some embodiments, a positioning unit is of a size, shape and position to form a space of a predetermined volume adjacent to the second aperture and below a top face of the positioning unit. In some embodiments, the interior volume of the positioning unit and the second aperture is a predetermined volume for analysis. As illustrated in FIG. 7, a positioning unit 135 can have a size, position and shape to form a sample region 745 of a predefined volume in the area adjacent to the positioning unit 135, the second aperture 130, and the filter unit 720.

The medical-sample filtration device 100 includes a filter unit 720 affixed to the second aperture 130. The filter unit includes a filter. For example, the filter can be a size-exclusion filter. Some embodiments of a filter unit include a filter that is a size-exclusion membrane and a holder securing the membrane in place. Some embodiments of a filter unit include a size-exclusion membrane and a support structure adjacent to the membrane. In some embodiments, the filter unit includes a filter, a holder securing the filter in place, and a waste pad.

An immunoassay device including a sample addition region is secured to the medical-sample filtration device with a framework. FIG. 7 illustrates a framework 725 securing the liquid-impermeable container adjacent to an immunoassay device, the framework 725 including a first position with the second aperture 130 positioned adjacent to a waste region 705 of the immunoassay device and a second position with the filter unit 720 of the medical-sample filtration device 100 positioned adjacent to the sample addition region 730 of the immunoassay. FIG. 7 illustrates the first position of the framework 725 as position C, with the second aperture 130 of the container positioned adjacent to a waste region 705 of the immunoassay device. FIG. 7 further depicts the second position of the framework 725 as D, where the filter region 700 would be positioned adjacent to the sample addition region 730 of the immunoassay device (see FIG. 8).

The immunoassay device includes a filter region 700 including a waste region 705. A waste region can include a space of a size, shape and position for fluid collection. A waste region can include an absorbent material configured as a waste pad. The immunoassay device also includes an immunoassay region 710 where the biochemical features of the assay are located. The immunoassay region 710 includes an internal immunoassay structure, such as paper, membrane and related materials. A sample addition aperture 730 is positioned on the immunoassay region 710 adjacent to the framework 725. A framework 725 positions the medical-sample filtration device 100 adjacent to the waste region 705 or adjacent to the sample addition aperture 730 of the immunoassay region 710. The immunoassay device also includes a visualization region 740 at a position distal to the sample addition aperture 730. In some embodiments, a color change in the immunoassay structure 715 adjacent to the visualization region 740 indicates the results of an immunoassay during use.

The filter region 700 of the immunoassay device includes a waste region distal to the filter unit 720 of the medical-sample filtration device 100. The waste region can include a material of a size, shape and composition to retain a majority of the waste fluid that passes through the filter, for example in a waste pad 705. In some embodiments, the waste region of an immunoassay device is a liquid-impermeable container of a size, shape and position to retain any excess fluid that passes through the filter unit of the adjacent medical-sample filtration device.

A medical-sample filtration device can include a sample addition aperture in the wall of the container at a position adjacent to the first aperture; and a sample addition conduit affixed to an exterior surface of the container, surrounding the sample addition aperture. For example FIG. 7 includes a sample addition conduit 190 affixed to the container around a sample addition aperture positioned near the first aperture 125 of the container.

Figure 8:
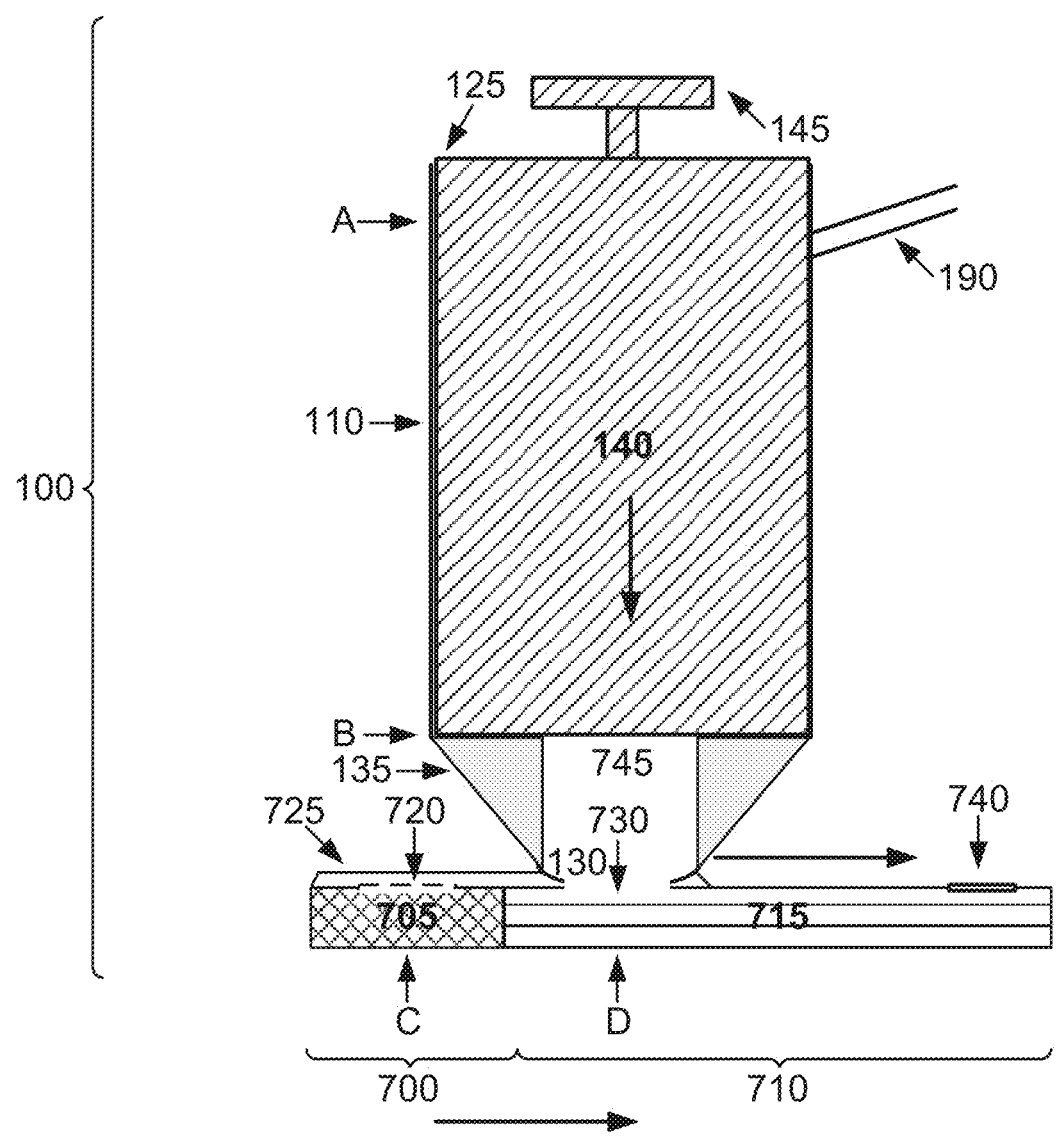
FIG. 8 is a schematic of a medical-sample filtration device.

FIG. 8 depicts an embodiment of a medical-sample filtration device 100 similar to the one illustrated in FIG. 7, the device 100 depicted in an alternate configuration. In the view shown in FIG. 8, the movable insert 140 has been pushed all the way down until it is in contact with the positioning unit 135. Subsequently, the medical-sample filtration device 100 has been moved along the framework 725 so that the second aperture 130 of the container is adjacent to the sample addition aperture 730 of the immunoassay device. In this position, any liquid sample present in the sample region 745 adjacent to the second aperture 130 of the container can move into the sample addition aperture 730 of the immunoassay device.

In some embodiments, the framework that secures a medical-sample filtration device to an immunoassay device includes: a first external housing surrounding a filter unit; a second external housing surrounding an immunoassay unit; and a hinge region affixed to both the first external housing and the second external housing, and positioned to move them adjacent to each other. In some embodiments, the immunoassay device is operably attached to the framework. In some embodiments, a piercing unit is affixed to the immunoassay device, the piercing unit positioned to breach a part of the immunoassay device when the first and second housings are positioned adjacent to each other by movement of the hinge region.

Figure 9:
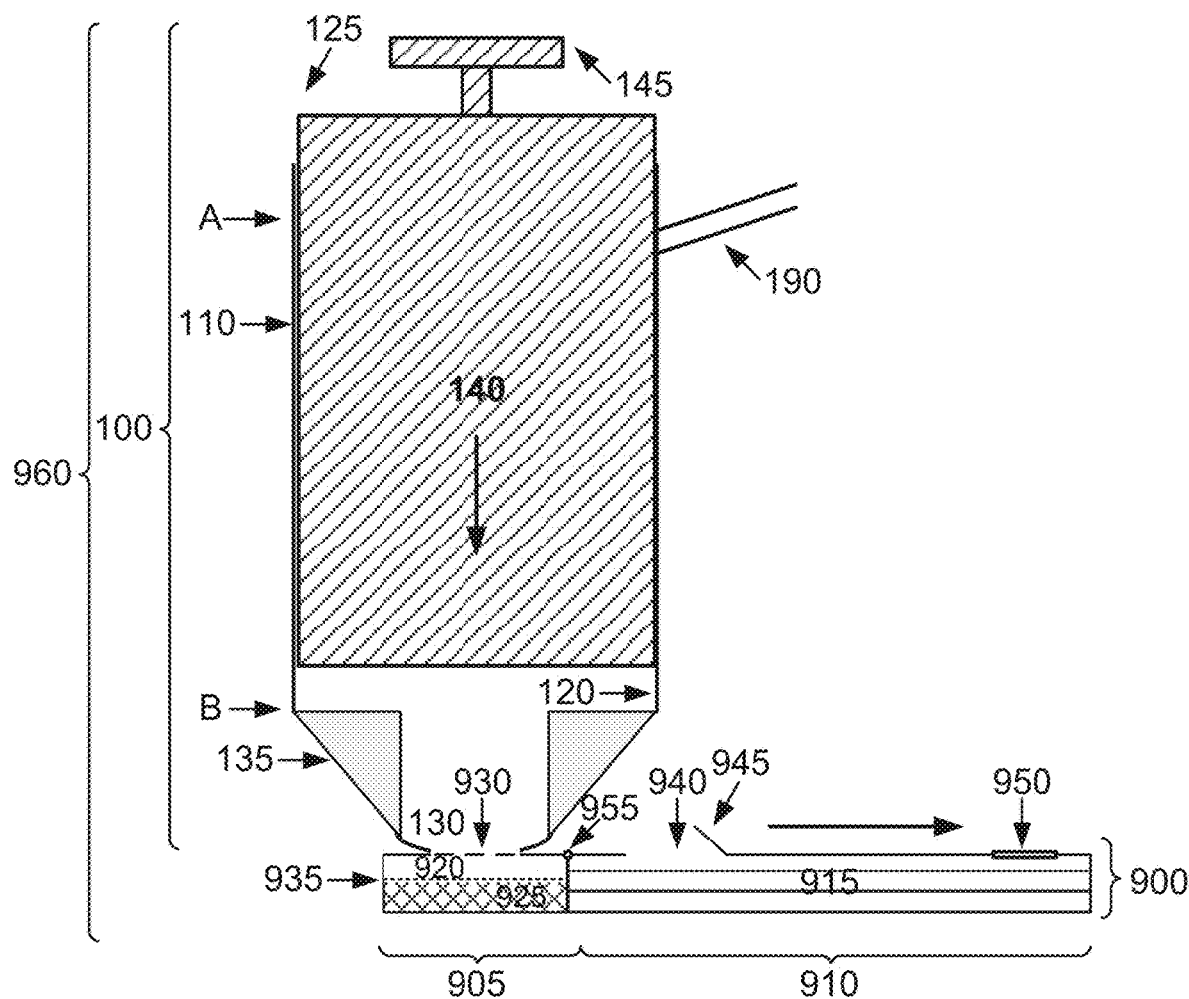
FIG. 9 is a schematic of a medical-sample filtration device.

FIG. 9 illustrates aspects of a medical-sample filtration device 100 and an immunoassay device 900 together forming an analysis unit 960. The medical-sample filtration device 100 is similar to those shown in FIGS. 1-8. The medical-sample filtration device 100 is affixed to an immunoassay device 900. The immunoassay device 900 includes a first external housing surrounding a filter unit 905 and a second external housing surrounding an immunoassay unit 910. A hinge region 935 connects the filter unit 905 to the immunoassay unit 910.

The filter unit 905 includes a filter 935 within the external housing of the unit. The filter can, for example, include a size-exclusion membrane. A sample region 920 is positioned on a first side of the filter 935, adjacent to the second aperture in the container of the medical-sample filtration device 100. A waste region 925 of the filter unit 905 is located on the other side of the filter 935 from the sample region 920. In some embodiments, a membrane 930 is fixed to an aperture in the filter unit 905 positioned to permit a fluid sample to enter the filter unit 905 from the medical-sample filtration device 100. The membrane 930 covering the aperture in the filter unit 905 is at a position adjacent to the second aperture 130 in the container of the medical-sample filtration device 100.

The immunoassay unit 910 of the immunoassay device 900 includes an external housing surrounding an immunoassay structure 915. A sample addition aperture 940 is positioned adjacent to one end of the immunoassay unit 910. A piercing unit 945 is affixed to the immunoassay unit 910 at a position adjacent to the sample addition aperture 940. A sample viewing area 950 is positioned adjacent to the distal end of the immunoassay unit 910.

During use, the movable insert 140 pushes down on a liquid sample present in the container and moves it through the membrane 9:30 into the filter unit 905. The liquid sample is further forced into the filter 935. When the filter 935 includes a size-exclusion membrane, liquid containing particles of an excluded size is retained in the sample region 920 and additional liquid is forced through the filter 935 into the waste region 925.

FIG. 10 depicts an embodiment of a medical-sample filtration device 100 and an immunoassay device 900 similar to the ones shown in FIG. 9. In this illustration, the medical-sample filtration device 100 and the immunoassay device 900 have been separated. During use, it is expected that the separation would occur after the medical-sample filtration device 100 had been used to force a fluid sample, such as urine, into the filter unit 905 of the immunoassay device 900. The medical-sample filtration device 100 can, for example, be of a size, shape and position to force a fluid sample through the membrane 903 and filter 935 of the filter unit 905. Excess fluid will be forced into the waste region 925 of the filter unit 905. Filtered sample, which can include an enriched proportion of analytes excluded from a filter that includes a size-exclusion membrane, will be retained in the sample region of the filter unit. The hinge 955 of the immunoassay device 900 can change position to bend the filter unit 905 and the immunoassay unit 910 adjacent to each other. The piercing unit 945 is positioned to intersect the membrane 930 of the filter unit 910 when the units are adjacent to each other.

Figure 11:
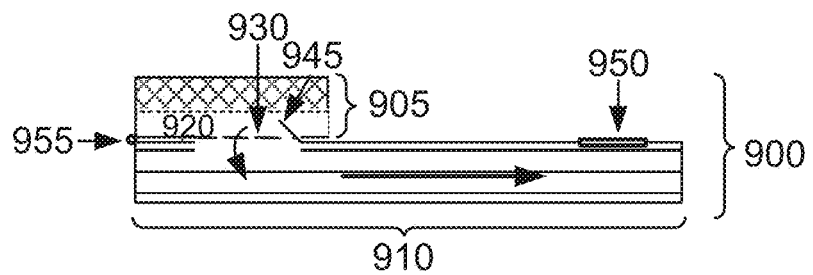
FIG. 11 is a schematic of a medical-sample filtration device.

FIG. 11 depicts an immunoassay device 900 similar to the ones shown in FIGS. 9 and 10. In the view of FIG. 11, the filter unit 905 and the immunoassay unit 910 are positioned with their long faces adjacent to each other after turning of the hinge 955. The piercing unit 945 has created a break in the membrane 930 covering the aperture in the filter unit 905. The break in the membrane permits fluid sample to flow from the sample region 920 into the immunoassay unit 910. After the immunoassay has completed, a result will be visible to a user in the sample viewing area 950.

Some embodiments of a medical-sample filtration device include: a liquid-impermeable container including at least one wall forming an internal surface with substantially even cross-sectional dimensions, a first aperture adjacent to a first end of the at least one wall; and a second aperture adjacent to a second end of the at least one wall; a movable insert positioned within the container, the movable insert including an external surface of a size and shape to reversibly mate with the internal surface of the container, the movable insert including a surface of a size, shape and position to transmit force along an axis of the movable insert in a direction from the first aperture to the second aperture; a positioning unit affixed to the internal surface of the container at a location adjacent to the second aperture; a conduit affixed to the second aperture of the container; a filter unit affixed to the conduit; a frangible cover forming a liquid-impermeable seal over an end of the conduit distal to the filter unit; and a piercing conduit, the piercing conduit including a first end affixed to a surface of the movable insert; and a second end including a piercing surface positioned to traverse the frangible cover.

Figure 12:
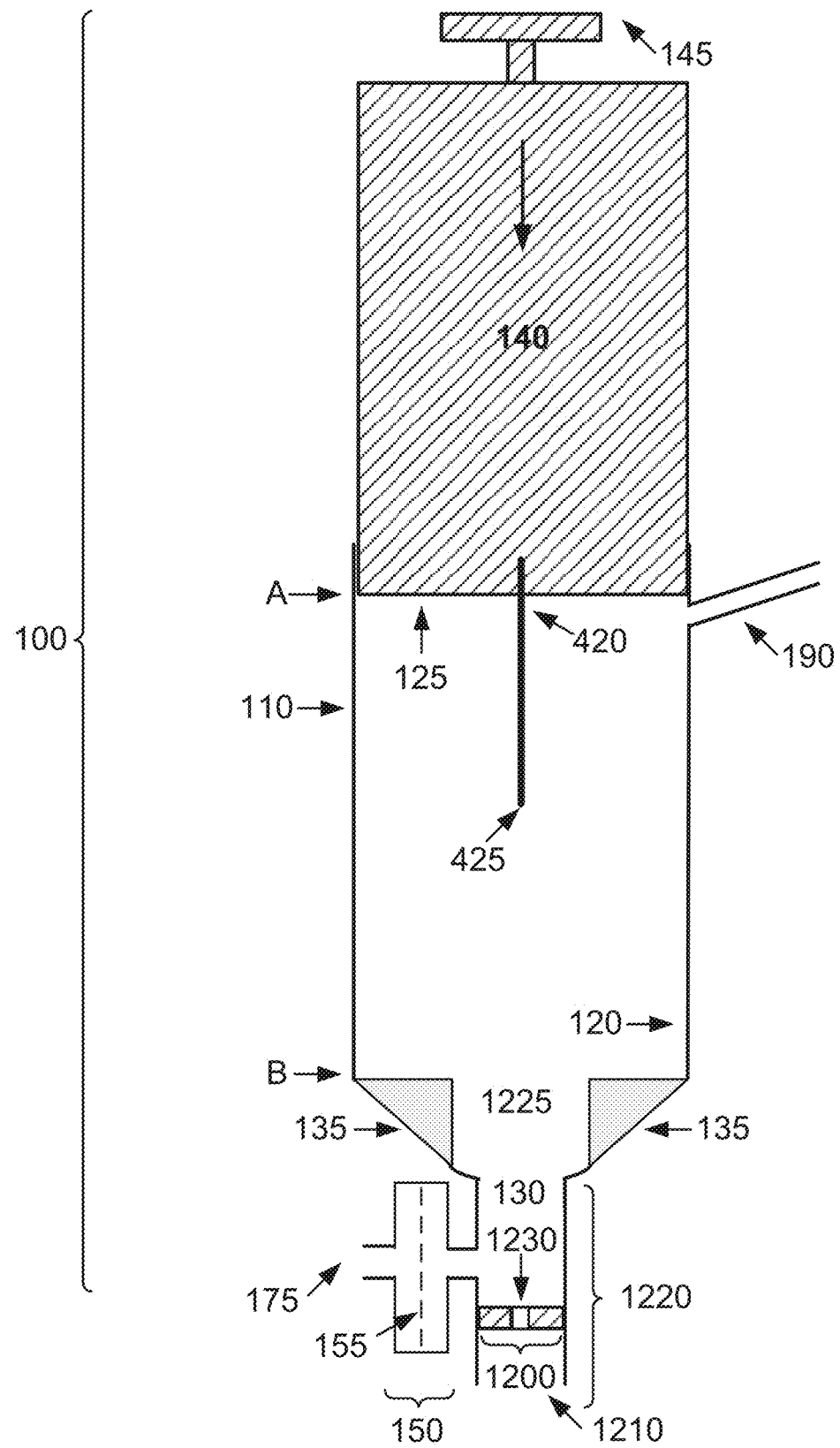
FIG. 12 is a schematic of a medical-sample filtration device.

FIG. 12 depicts a medical-sample filtration device 100 including a liquid-impermeable container including a wall 110 forming an internal surface 120 with substantially even cross-sectional dimensions. In the embodiment illustrated, the container is roughly a cylindrical structure. The medical-sample filtration device 100 includes a first aperture 125 adjacent to a first end of the wall 110 of the container, and a second aperture 130 adjacent to a second end of the wall 110. There is a movable insert 140 positioned within the container. The movable insert 140 includes an external surface of a size and shape to reversibly mate with the internal surface 120 of the container. The movable insert 140 includes a surface of a size, shape and position to transmit force along an axis of the movable insert 140 in a direction from the first aperture 125 to the second aperture 130, or vertically in the view of FIG. 12. The medical-sample filtration device 100 includes a positioning unit 135 affixed to the internal surface 120 of the container at a location adjacent to the second aperture 130. The medical-sample filtration device 100 includes a conduit 1220 affixed to the second aperture 130 of the container. A filter unit 150 is affixed to the conduit 1220. There is a frangible cover 140 forming a liquid-impermeable seal 1200 over an end 1210 of the conduit 1220 distal to the filter unit 150. A piercing conduit 420 has a first end affixed to a surface of the movable insert 140, and a second end including a piercing surface 425 positioned to traverse the frangible cover 140. A sample addition aperture is positioned in the wall of the container adjacent to the first aperture 125 and a sample addition conduit 190 is affixed to an exterior surface of the container, at a location surrounding the sample addition aperture.

The medical-sample filtration device 100 includes a container with an internal surface 120 that is a cylindrical structure. The internal surface 120 is a substantially smooth internal surface. Correspondingly, the external surface of the movable insert 140 is shaped as a cylindrical structure. The external surface of the movable insert 140 is of a size and shape to reversibly mate with the internal surface 120 of the container. The movable insert 140 includes a pressure application region 145 of a size, shape and position to transmit force against a surface of the movable insert 140 and along an axis of the insert 140 substantially parallel with the internal surface 120 of the container. In some embodiments, the movable insert is of a size, shape and position to transmit a force of at least 50 psi toward the second aperture (i.e. substantially vertically in the view of FIG. 12).

The medical-sample filtration device 100 includes a positioning unit 135. The positioning unit 135 is affixed to the interior surface of the container at a position adjacent to the second aperture 130 in the container. In some embodiments, a positioning unit includes a top face of a size and shape to mate with an exterior surface of the movable insert. For example, the top face of the positioning unit can include a surface of a size, shape and position to mate with a lower surface of a movable insert. In some embodiments, a positioning unit is of a size, shape and position to form a space of a predetermined volume adjacent to the positioning unit. For example in the embodiment illustrated in FIG. 12, the positioning unit 135 forms a space 1225 in combination with the interior of the conduit 1220 adjacent to the impermeable seal 1200.

In some embodiments, the conduit includes a first end affixed to the second aperture of the container; and a second end affixed to the frangible cover. In the embodiment shown in FIG. 12, the conduit 1220 includes a first end affixed to the second aperture 130 of the container; and a second end 1210 affixed to the frangible cover 1200, with a filter unit 150 affixed to an edge of the conduit 1220 in a position between the first end and the second end 1210. In the embodiment shown, the filter unit 150 is affixed to the side of the conduit 1220. In some embodiments, the conduit is a tubular structure.

A medical-sample filtration device includes a filter unit affixed to the conduit. The filter unit is of a size, shape, position and composition to filter liquid forced through the second aperture of a container by movement of a movable insert. In some embodiments, a filter unit is attached to the side of the conduit. For example, FIG. 12 depicts an embodiment wherein the filter unit 150 is affixed to the side of the conduit 1220; and wherein the filter unit 150 includes a filter 155 with a surface facing the attachment between the conduit 1220 and the filter unit 150. The embodiment also includes a waste conduit 175 attached to the filter unit 150 at a position distal to the conduit 1220. In some embodiments, a filter unit includes a filter; and a holder securing the filter in place. In some embodiments, a filter unit includes an attachment conduit connecting the filter unit to the conduit. In some embodiments, a filter unit includes a size-exclusion membrane; and a holder securing the membrane in place. In some embodiments, a filter unit includes a size-exclusion membrane; and a support structure adjacent to the membrane.

The medical-sample filtration device includes a frangible cover forming a liquid-impermeable seal over an end of the conduit distal to the filter unit. In the embodiment shown in FIG. 12, there is a frangible cover 1230 within an impermeable seal 1200 adjacent to the end 1210 of the conduit 1220. In some embodiments, the frangible cover is of a size, shape and position to be breached by the piercing conduit. For example, FIG. 12 depicts the frangible cover 1230 within the impermeable seal 1200 positioned to intersect with the piercing conduit 420 when the movable insert 140 is adjacent to the positioning unit 135 (see also FIG. 13). In some embodiments, the interior volume of the container adjacent to the positioning unit, the conduit, and the filter unit on the adjacent side to the conduit is a volume corresponding to a predicted analysis sample volume. The interior volume of the interior volume of the container adjacent to the positioning unit, the conduit, and the filter unit can form a volume corresponding to a predicted analysis sample volume for a downstream assay such as a particular immunoassay.

Figure 13:
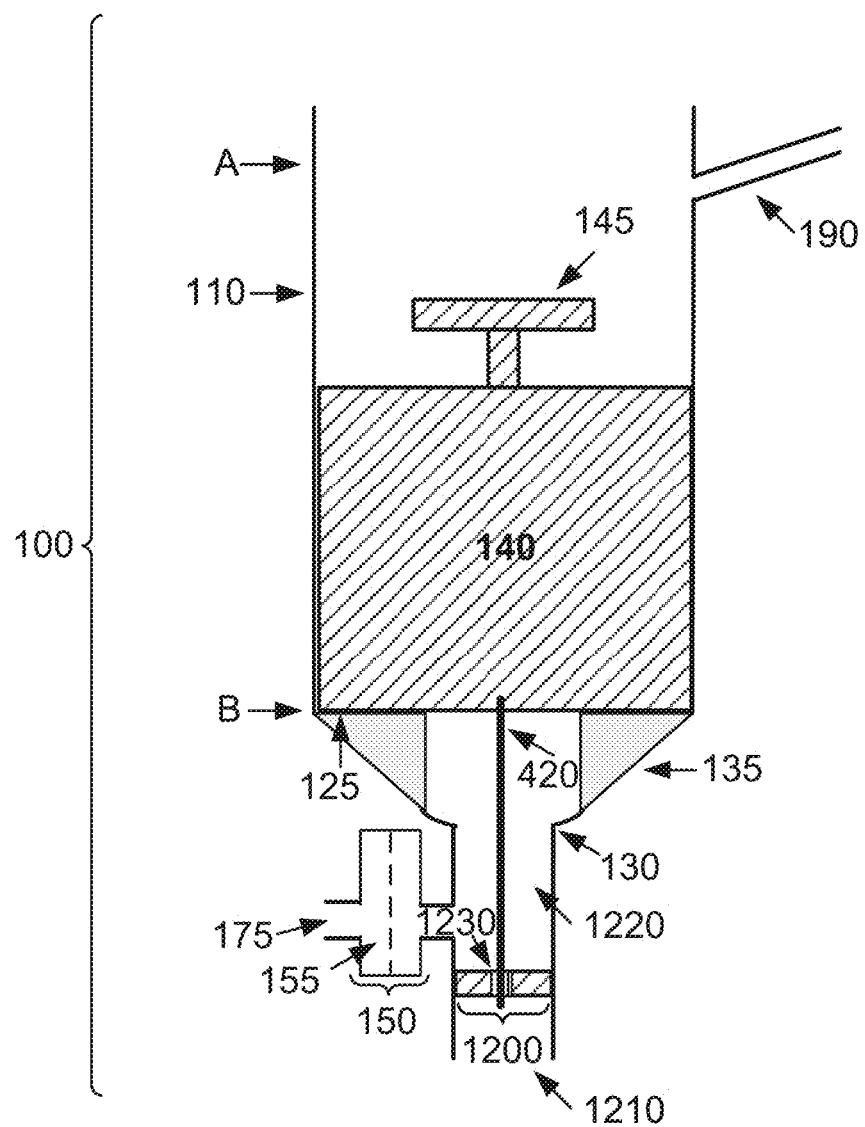
FIG. 13 is a schematic of a medical-sample filtration device.

In some embodiments, the piercing conduit is of a size, shape and position so that the piercing surface of the piercing conduit traverses the frangible cover when the movable insert is in contact with the positioning unit. For example, FIG. 13 depicts an embodiment similar to the one illustrated in FIG. 12, with the movable insert 140 at a lower position within the container so that the bottom face of the movable insert 140 is in contact with a top surface of the positioning unit 135. The piercing conduit 420 is of a size, shape and position so that it traverses the length of the conduit 1220 between the lower surface of the movable insert 140 and the impermeable seal 1200. The piercing conduit 420 traverses the frangible cover 1230 within the impermeable seal 1200 so that the piercing surface 425 is positioned at the distal side of the frangible cover 1230 from the movable insert 140. In this configuration, the frangible cover 1230 within the impermeable seal 1200 is breached and a fluid can exit the conduit 1220 through the second end 1210. In some embodiments, the second end is functionally attached to an immunoassay device.

Figure 14:
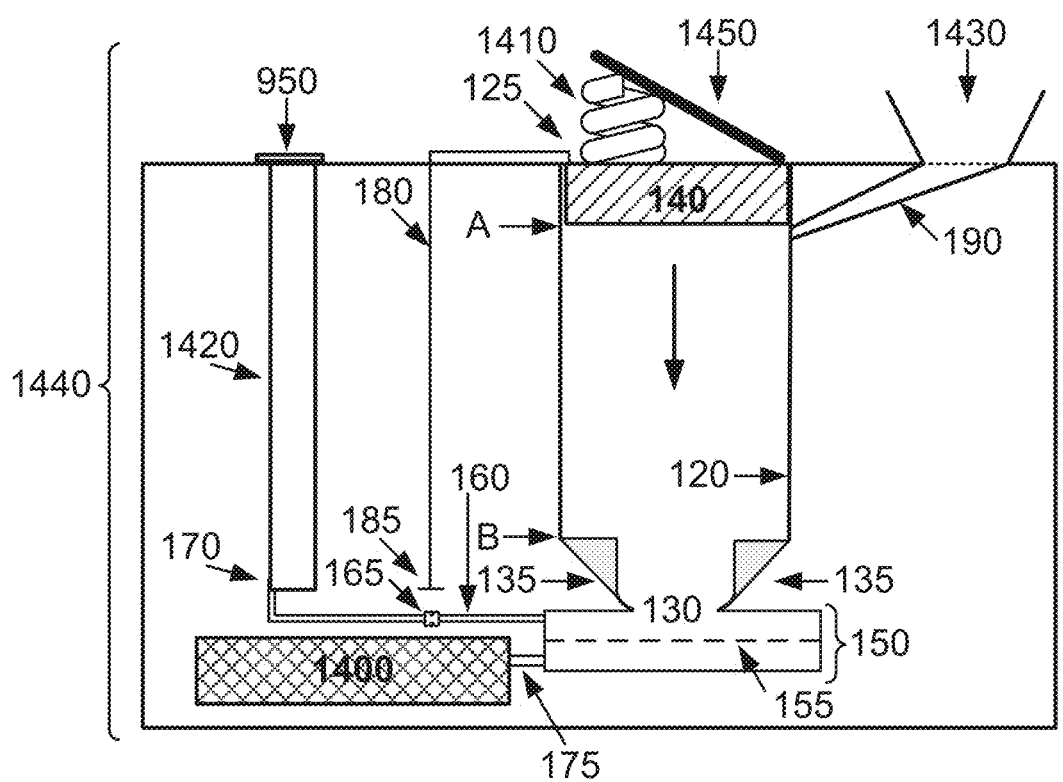
FIG. 14 is a schematic of a medical-sample filtration device.

In some embodiments, a medical-sample filtration device is integrated with an immunoassay within a unified housing. This can be of benefit, for example, for ease of use, common disposal, and minimal packaging during transport and storage. FIG. 14 depicts an embodiment of a combined medical-sample filtration and immunoassay device 1440. The device 1440 includes a container similar to the ones previously described herein, with an internal surface 120 of a size and shape to mate with the outer surface of a movable insert 140 within the container. A sample conduit 190 is attached to the side of the container and positioned to carry a liquid medical sample from a sample addition region 1430 to the interior of the container. The container is an appropriate size to hold a liquid medical sample for analysis. For example if the liquid medical sample is urine to be analyzed for LAM in an immunoassay, the starting sample volume can be between 50 mL to 300 mL. The container has a first aperture 125 and a second aperture 130. A positioning unit 135 is attached to the interior of the container adjacent to the second aperture 130. A filter unit 150 including a filter 155 that is a size-exclusion membrane is positioned within the filter unit. A waste conduit 175 attached on an end to a waste region 1400 is attached on an opposite end to the filter unit 150 at a position distal to the container.

The integrated device illustrated in FIG. 14 includes a pressure plate 1450 affixed to one side of the aperture 125 with a hinge or similar fastener. A force transmission element, such as spring 1410 is positioned between the pressure plate 1450 and the top surface of the movable insert 140. The device is used starting in a configuration like that illustrated in FIG. 14. During use, a medical sample can be added to the sample addition region 1430, where it passes through the addition conduit 190 and into the interior of the container. Once the sample is loaded into the interior volume of the container, a user (for example, a nurse or clinicians can press down on the pressure plate 1450. In some embodiments, a force of at least 50 psi is required at the filter 155 surface to drive the fluid through a filter 155 that is a size-exclusion membrane within a reasonable time frame as a clinical use parameter for the complete sample analysis (e.g. under 1 hour). The integrated device can be of a size, shape and composition so that a user can place the integrated device on a level surface, such as a hard floor, and step down on the pressure plate 1450 to achieve the desired force. The force from the pressure plate 1450 is transmitted via the force transmission element, for example spring 1410 on to the top surface of the movable insert 140. The movable insert 140 moves within the container to a position where the lower surface of the movable insert 140 is in contact with the upper surface of the positioning unit 135. For example FIG. 14 depicts a first position for the lower surface of the movable insert 140 as "A" and a second position for the lower surface of the movable insert as "B." The fluid within the container volume is therefore filtered through the filter 155. Excess fluid flows through the waste conduit 175 into a waste region 1400. Fluid that does not go through the filter 155, including analytes that are a greater size than the size-exclusion membrane within the filter unit 150, are trained within the volume defined b lower face of the movable insert 140, the sides of the positioning unit 135, the volume of the filter unit prior to the filter 155, and the first portion of the sample conduit 160 prior to the valve unit 165.

The movable insert 140 is attached to a connector 180. The connector includes a pressure transmitting plate 185 at the distal end from the attachment to the movable insert 140. When the movable insert 140 has moved to its full extent within the container (e.g. position "B"), the pressure transmitting plate 185 pushes against the exterior surface of a valve unit 165 attached to the sample conduit 160. The valve unit 165 includes a binary mechanism configured to open the valve within the valve unit 165 in response to pressure from the pressure transmitting plate 185. Filtered sample, which is expected to be enriched for analytes of interest, can then flow through the sample dispensation end 170 of the sample conduit 160 and into the sample addition region of an immunoassay 1420. For example, the immunoassay can include a paper or membrane based immunoassay. For example, the immunoassay can include a lateral flow assay (LFA). After the immunoassay has finished operating, a user can see a visual display of the results, for example one or more colored lines, in the sample viewing area 950 of the device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A medical-sample filtration device comprising:
   a liquid-impermeable container including at least one wall forming an internal surface with a least one constant cross sectional dimension, a first aperture adjacent to a first end of the at least one wall, and a second aperture adjacent to a second end of the at least one wall;
   a movable insert positioned within the container, the movable insert including an external surface of a size and shape that is in reversible mateable contact with the internal surface of the container;
   a positioning unit affixed to the internal surface of the container at a location adjacent to the second aperture;
   a filter unit affixed to the second aperture;
   a sample conduit affixed to the filter unit;
   a valve unit, including a valve with an open-close switch, operably attached to the sample conduit; and
   a connector operably connected between the movable insert and the valve unit, the connector operable to close the valve when the movable insert is in a predefined position relative to the container.

2. The medical-sample filtration device of claim 1, wherein the movable insert comprises: a pressure application region of a size, shape and position to transmit force against a surface of the movable insert and along an axis of the insert parallel with the external surface of a size and shape to reversibly mate with the internal surface of the container.

3. The medical-sample filtration device of claim 1, wherein the movable insert is of a size, shape and position to transmit a force of at least 50 psi toward the second aperture.

4. The medical-sample filtration device of claim 1, wherein the filter unit comprises: a filter; and a holder securing the filter in place; wherein the sample conduit is affixed to the filter unit at a position between the filter and the second aperture of the container.

5. The medical-sample filtration device of claim 1, wherein the filter unit comprises: a size-exclusion membrane; and a holder securing the membrane in place.

6. The medical-sample filtration device of claim 1, wherein a volume for analysis is defined by an interior volume within the container defined by the positioning unit, an interior volume of the filter unit, and an interior volume of the sample conduit between the filter unit and the valve unit.

7. The medical-sample filtration device of claim 1, further comprising: a sample addition aperture in the wall of the container at a position adjacent to the first aperture; and a sample addition conduit affixed to an exterior surface of the container, surrounding the sample addition aperture.

8. The medical-sample filtration device of claim 1, further comprising: a fluid metering container affixed to the sample conduit distal to the valve, wherein the fluid metering container includes an internal region of a size to contain a sample volume, and an overflow conduit positioned to remove excess fluid from the internal region.

9. The medical-sample filtration device of claim 1, further comprising: an immunoassay operably attached to the sample conduit.

\* \* \* \* \*